United States Patent
Stemmer

(10) Patent No.: US 8,461,837 B2
(45) Date of Patent: Jun. 11, 2013

(54) MAGNETIC RESONANCE METHOD AND APPARATUS WITH DISPLAY OF DATA ACQUISITION PROGRESS FOR A SUBJECT CONTINUOUSLY MOVING THROUGH THE APPARATUS

(75) Inventor: Alto Stemmer, Abenberg (DE)

(73) Assignee: Siemens Aktiengesellschaft, Munich (DE)

( * ) Notice: Subject to any disclaimer, the term of this patent is extended or adjusted under 35 U.S.C. 154(b) by 484 days.

(21) Appl. No.: 12/763,330

(22) Filed: Apr. 20, 2010

(65) Prior Publication Data

US 2010/0264924 A1 Oct. 21, 2010

(30) Foreign Application Priority Data

Apr. 20, 2009 (DE) .......................... 10 2009 017 775

(51) Int. Cl.
*G01V 3/00* (2006.01)
(52) U.S. Cl.
USPC ............................ 324/306; 324/307; 600/420
(58) Field of Classification Search
USPC ............................ 324/306, 307, 309; 600/420
See application file for complete search history.

(56) References Cited

U.S. PATENT DOCUMENTS 5,713,358 A * 2/1998 Mistretta et al. ............. 600/420
7,570,985 B2 * 8/2009 Takabayashi et al. ........ 600/420

OTHER PUBLICATIONS

"Interactive Continuously Moving Table (iCMT) Large Field-of-View Real-Time MRI," Sabati et al, Magnetic Resonance in Medicine, vol. 55 (2006) pp. 1202-1209.
"Long Field-of-View MRI Using Continuous Table Motion," Riederer et al, World Automation Congress (2004) pp. 81-86.
"Sliding Multislice (SMS): A New Technique for Minimum FOV Usage in Axial Continuously Moving-Table Acquisitions," Fautz et al, Magnetic Resonance in Medicine, vol. 55 (2006) pp. 363-371.
"Principles of Whole-Body Continuously-Moving-Table MRI," Börnert et al, Journal of Magnetic Resonance Imaging, vol. 28 (2008) pp. 1-12.
"Sliding Multislice MRI for Abdominal Staging of Patients With Pelvic Malignancies: A Pilot Study," Sommer et al, Journal of Magnetic Resonance Imaging, vol. 27 (2008) pp. 666-672.

* cited by examiner

*Primary Examiner* — Louis Arana
(74) *Attorney, Agent, or Firm* — Schiff Hardin LLP

(57) ABSTRACT

In a method and magnetic resonance apparatus to display progress of the acquisition of measurement data of an examination region of an examination subject during continuous travel of the examination region through a magnetic resonance apparatus, a current projection image is calculated on the basis of current measurement data acquired from central k-space during the continuous travel of the examination region, and the currently calculated projection image is displayed. By the calculation of the projection images on the basis of measurement data from central k-space, this calculation can ensue particularly quickly and with little effort. A particularly fast display of the projection images is therefore possible. A projection image can be calculated particularly quickly and simply from measurement data along a central k-space line—i.e. a k-space line that runs through the center of k-space—using a one-dimensional Fourier transformation along this central k-space line.

9 Claims, 8 Drawing Sheets

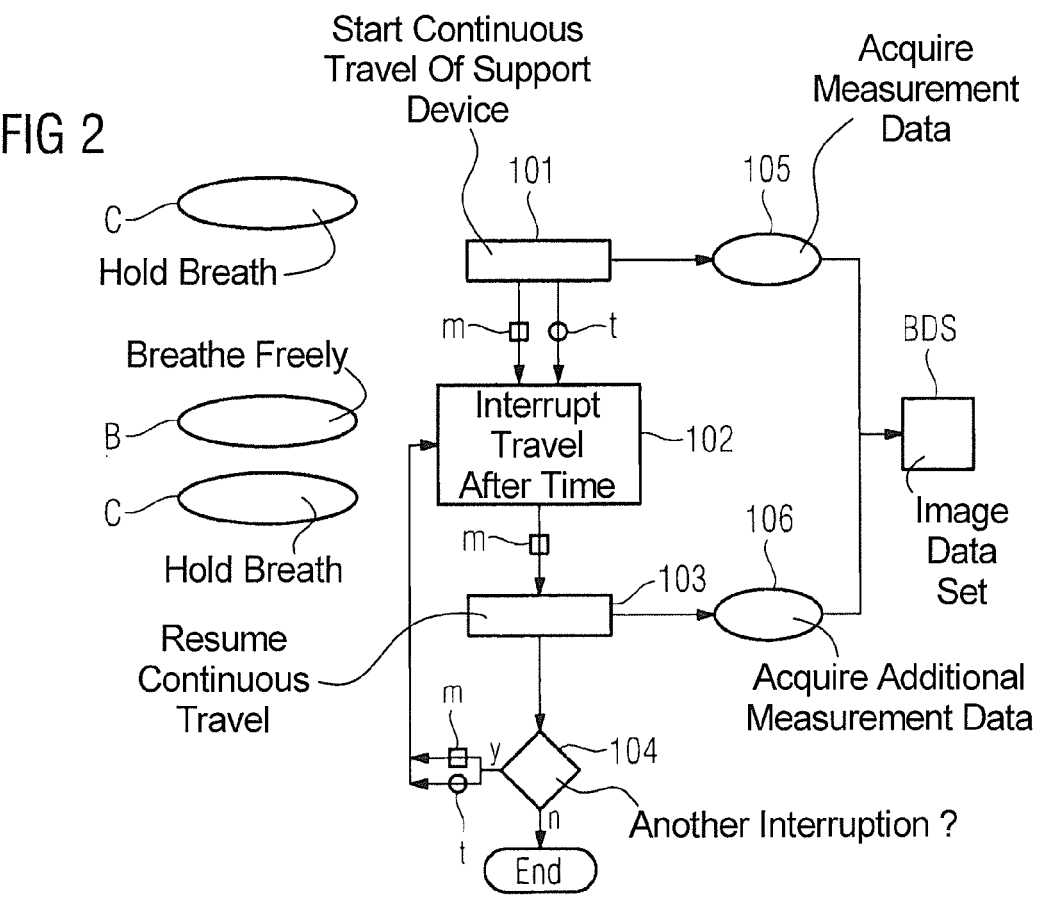
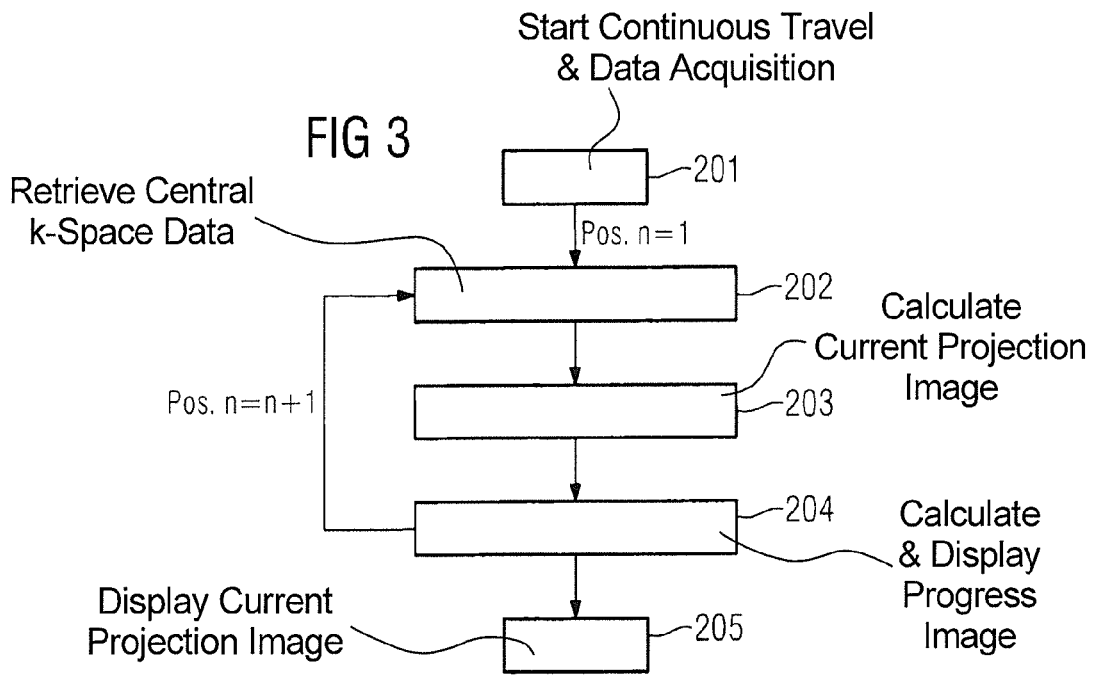

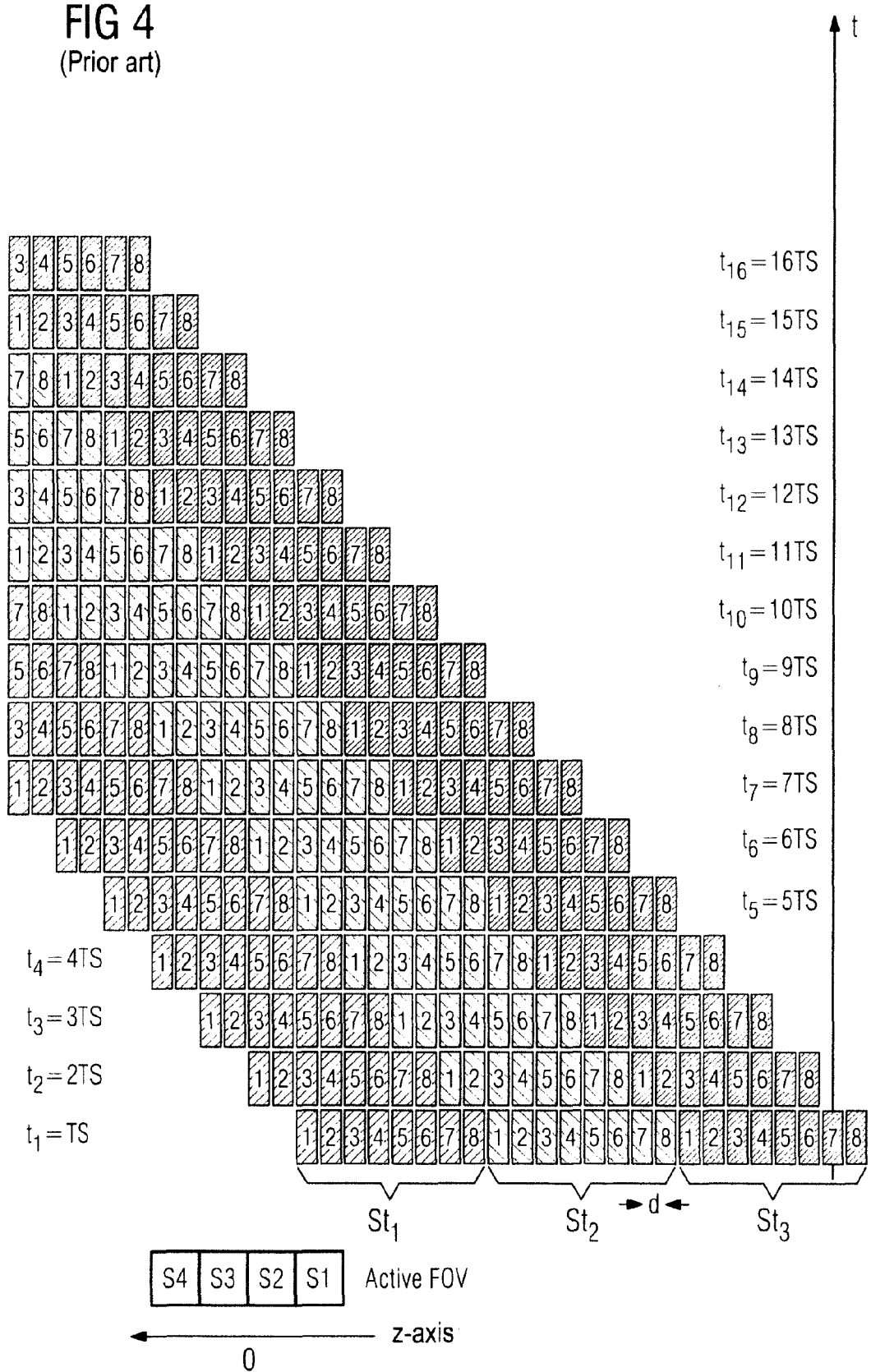

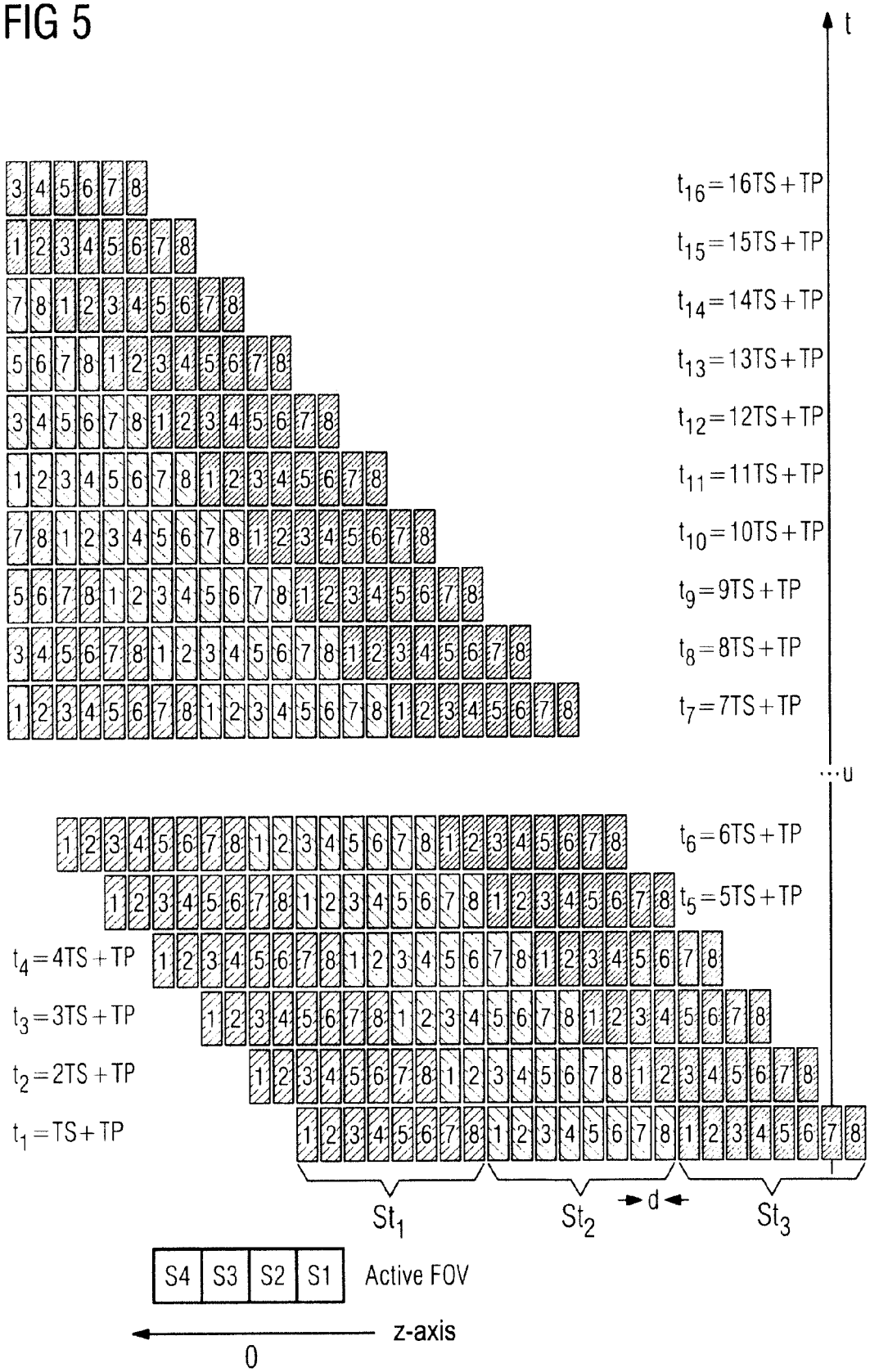

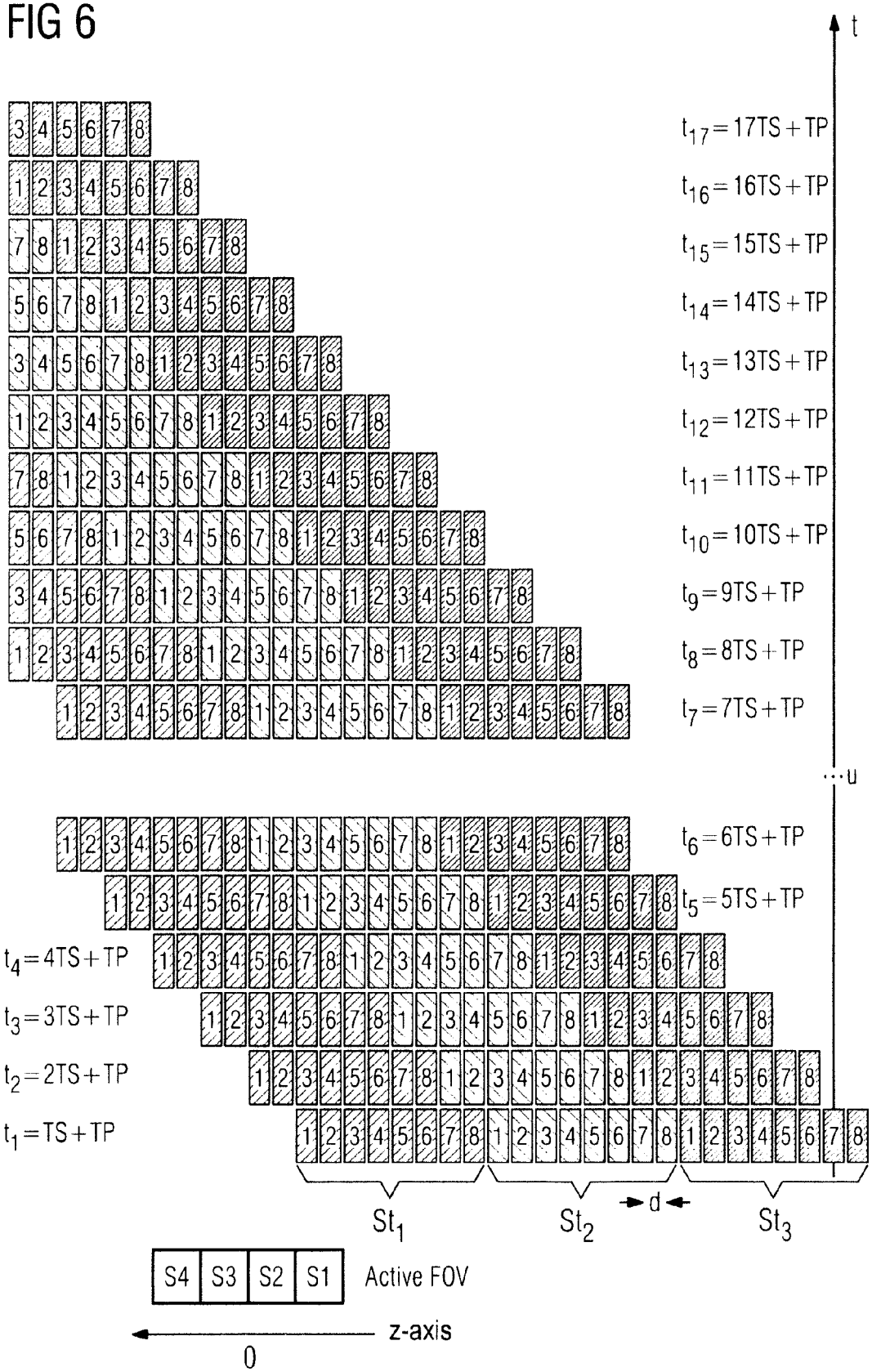

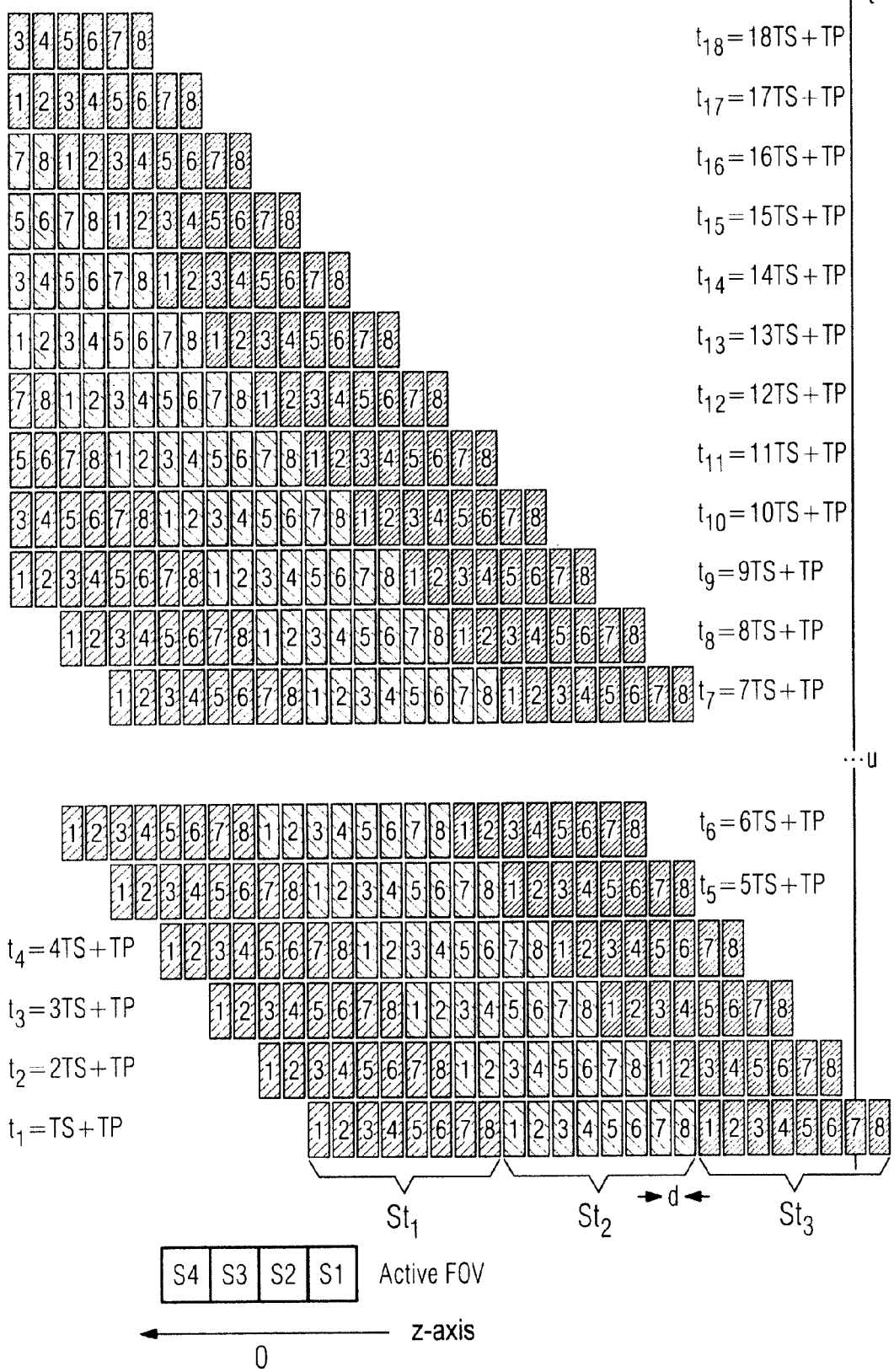

FIG 10
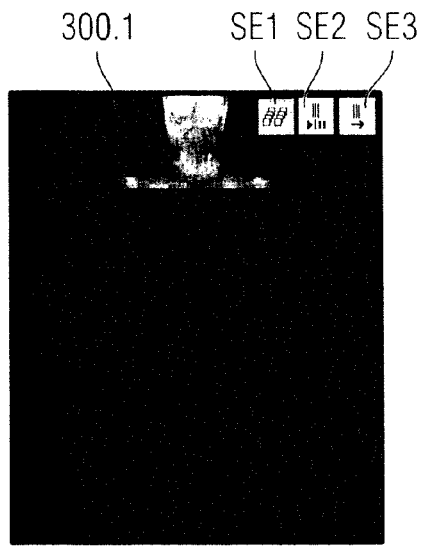
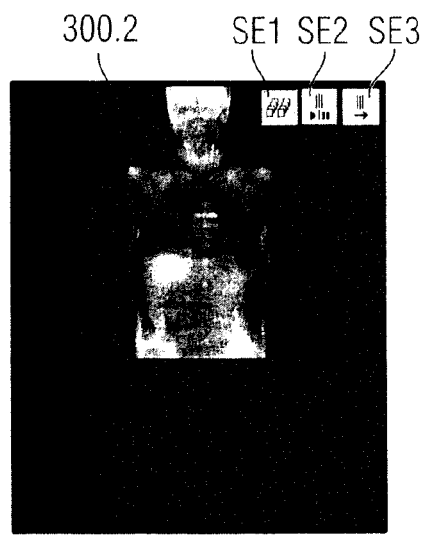
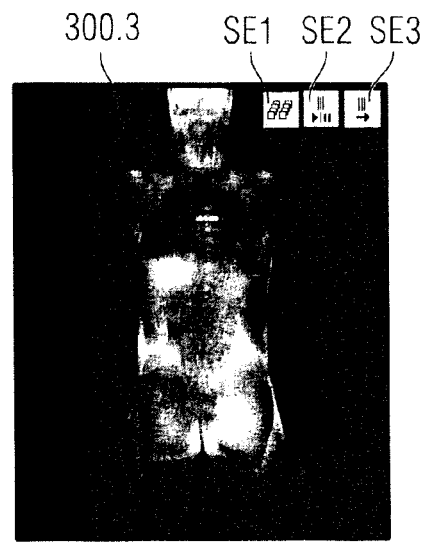

MAGNETIC RESONANCE METHOD AND APPARATUS WITH DISPLAY OF DATA ACQUISITION PROGRESS FOR A SUBJECT CONTINUOUSLY MOVING THROUGH THE APPARATUS

BACKGROUND OF THE INVENTION

1. Field of the Invention

The present invention concerns a method, a magnetic resonance apparatus and a computer-readable storage medium to display the progress of the acquisition of measurement data from an examination region of a patient during continuous travel of the examination region through the magnetic resonance apparatus.

2. Description of the Prior Art

Magnetic resonance (MR) is a known modality with which images of the inside of an examination subject can be generated. Expressed simply, the examination subject is positioned in a comparably strong, static, homogeneous basic magnetic field (field strengths of 0.2 Tesla to 7 Tesla or more) in a magnetic resonance apparatus so that its nuclear spins orient along the basic magnetic field. Radio-frequency excitation pulses are radiated into the examination subject, that cause the nuclear spins to behave so as to emit magnetic resonance signals that are measured and MR images are reconstructed based thereon. For spatial coding of the measurement data, rapidly-switched (activated) magnetic gradient fields are superimposed on the basic magnetic field. The acquired measurement data are digitized and stored as complex numerical values in a k-space matrix. An associated MR image can be reconstructed from the k-space matrix populated with such values, for example by means of a multidimensional Fourier transformation. The examination subject can be living (for example an animal or a patient) or inanimate (for example a sample or a phantom).

Magnetic resonance apparatuses with a support device (for example a patient bed) that can be automatically driven into and out of a patient receptacle (by means of a drive device) of the magnetic resonance apparatus that is permeated by a magnetic field of the magnetic resonance apparatus are known for the acquisition of magnetic resonance images. Since the patient receptacle frequently has a quite small diameter, the patient is placed on the patient bed outside of the patient receptacle, after which the patient bed can be automatically driven into the patient receptacle by means of the drive device.

The patient or another examination subject is briefly, continuously driven through the magnetic resonance apparatus by means of the support device during the acquisition of the measurement data from an examination region of the patient, or the examination subject. The measured "field of view" (FOV) can be expanded in the direction of the travel direction of the support device by controlling the movement of the support device, so examination regions that are larger in the direction of the travel direction of the support device than the measurement volume of the magnetic resonance apparatus can be examined. For example, whole-body acquisitions of patients can be generated in one measurement pass. Conversely, the measurement volume in which optimally ideal measurement conditions are generated can be limited in the direction of the travel direction of the support device without limiting the total achievable FOV.

Applied techniques for such an acquisition of measurement data can be roughly subdivided into two-dimensional (2D) axial measurements with the travel direction of the support device perpendicular to the readout direction of the measurement data, and three-dimensional (3D) techniques in which the readout direction of the measurement data is oriented parallel to the travel direction of the support device. An overview of such techniques is provided in, for example, the article by Börnert and Aldefeld, "Principles of Whole-Body Continuously-Moving-Table MRI", Journal of Magnetic Resonance Imaging 28: 1-12 (2008).

Monitoring of the measurement in real time is desirable, in particular given such measurements with continuously moving examination region.

Techniques for generation of overview images in which, for example, the progress of the measurement can be superimposed on planning data are already known in this regard. Such overview images can, for example, be generated within the scope of what are known as prescans. However, the precision of such a monitoring of the progress of a measurement is only low since the actual progress is not monitored, rather a progress "according to plan".

Furthermore, techniques are known that display current MR data from current or previously acquired measurement data. For this purpose, a current overview image (for example) is calculated using what is known as a "maximum intensity projection" (MIP) from current MR images already reconstructed from the measurement data and is displayed to the operator as a projection image. However, it is disadvantageous that all measurement data must be acquired and processed for such a projection image, which leads to an increased reconstruction time for the current MR images and also the current overview images. The display of such a projection image can therefore normally not be implemented fast enough, in particular not in real time (i.e. simultaneously with the actual progress of the acquisition of the measurement data).

SUMMARY OF THE INVENTION

An object of the present invention is to provide a method, a magnetic resonance apparatus and a computer-readable storage medium that enables a monitoring of the progress of a measurement with examination region moving continuously in the magnetic resonance apparatus.

The method according to the invention for the display of a progress of an acquisition of measurement data of an examination region of a patient during a continuous travel of the examination region through a magnetic resonance apparatus includes the following steps: calculate a current projection image on the basis of current measurement data acquired from central k-space during the continuous travel of the examination region, and display the currently calculated projection image.

The calculation of the projection images on the basis of measurement data from central k-space can ensue particularly quickly and with little effort. A particularly fast display of the projection images is therefore possible. The projection image is calculated particularly quickly and simply from measurement data along a central k-space line (i.e. a k-space line that runs through the center of k-space) by a one-dimensional Fourier transformation along this central k-space line.

In an embodiment, a progress image is constructed and displayed from successive projection images calculated in series in the course of the continuous travel of the examination region. All previously calculated projection images are therefore displayed in a composite progress image, so a better overall impression of the previously occurred measurement is achieved.

The examination region is advantageously divided up into slices and the measurement data are acquired per slice. A projection image can thus be calculated for each slice of the examination region. If a progress image is constructed from such projection images, one slice in the examination region corresponds to one line in the progress image.

Lines of the progress image can be pre-populated with a pixel value of zero until a projection image corresponding to the line is calculated and the progress image is further constructed in that the line is filled with pixel values of the projection image. The size of the progress image is hereby maintained overall and the portion of the progress image that has already been constructed from projection images "grows" in the course of the measurement with the progress of the measurement.

A magnetic resonance apparatus according to the invention is fashioned to acquire measurement data of an examination region of a patient during a continuous travel of the examination region through the magnetic resonance apparatus and has a support device that can travel through the magnetic resonance apparatus, a support device control unit with which movement of the support device is controlled, a computer configured to implement the method as described above, and a display device that displays images generated from the acquired measurement data.

A computer-readable storage medium according to the invention is encoded with programming code/instructions that cause the method as described above to be implemented when the storage medium is loaded into a computer that is connected with a magnetic resonance apparatus, and the programming code is executed on the computer.

The advantages and embodiments listed with regard to the method analogously apply to the magnetic resonance apparatus and the computer program.

BRIEF DESCRIPTION OF THE DRAWINGS

FIG. 2 is a flowchart of an exemplary embodiment of a method to acquire measurement data from an examination region of a patient during continuous travel of the examination region through a magnetic resonance apparatus for the generation of an image data set.

FIG. 3 is a flowchart of the method to display a progress of an acquisition of measurement data of an examination region of a patient during a continuous travel of the examination region through a magnetic resonance apparatus.

FIG. 4 is an illustrative diagram of the SMS technique.

FIGS. 5-7 are illustrative diagrams for various exemplary embodiments of the method to acquire measurement data of an examination region of a patient during a continuous travel of the examination region through a magnetic resonance apparatus for the generation of an image data set.

FIG. 10 show exemplary progress images at different times during the continuous travel.

DESCRIPTION OF THE PREFERRED EMBODIMENTS

Figure 1:
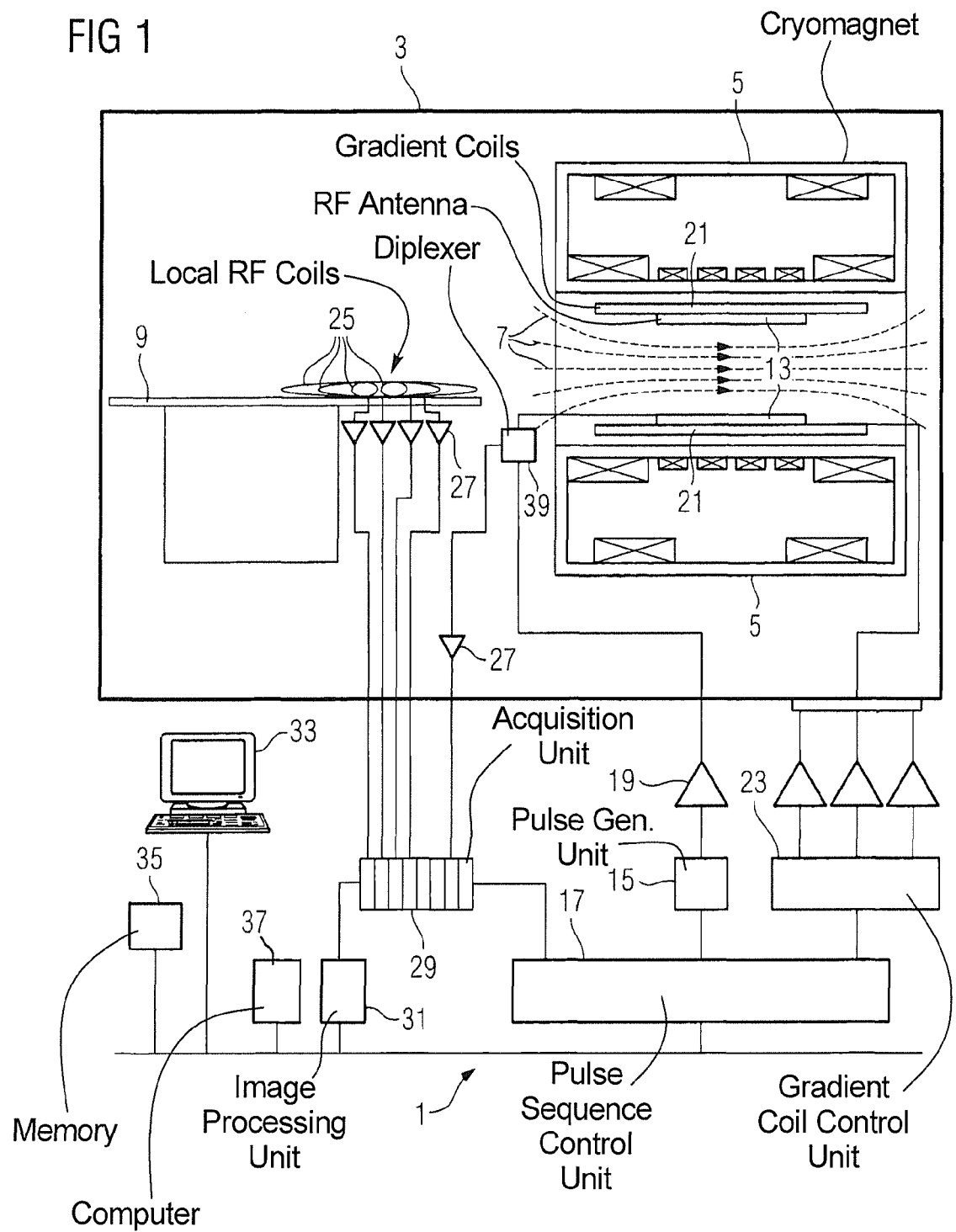
FIG. 1 schematically illustrates a magnetic resonance apparatus.

FIG. 1 schematically shows the basic design of a magnetic resonance apparatus 1. In order to examine a body by means of MR imaging, different magnetic fields that are matched to one another as precisely as possible in terms of their temporal and spatial characteristics are radiated into the body.

A strong magnet (typically a cryomagnet 5 with a tunnel-shaped opening) that is arranged in a measurement chamber 3 shielded against radio frequencies generates a static, strong basic magnetic field 7 that typically amounts to 0.2 Tesla to 7 Tesla or more. An examination subject to be examined (for example a patient; not shown here) is borne on a support device 9 (for example a patient bed) that can be moved through the magnetic resonance apparatus and is positioned in the homogeneous region of the basic magnetic field 7 for an examination. Movement of the support device 9 is controllable by a support device control unit 31 of the magnetic resonance apparatus 1.

The excitation of nuclear spins in the examination subject ensues by magnetic radio-frequency excitation pulses that are radiated by at least one radio-frequency antenna, represented here for example as a body coil 13. The radio-frequency excitation pulses are generated by a pulse generation unit 15 that is controlled by a pulse sequence control unit 17. After an amplification by a radio-frequency amplifier 19, they are conducted to the at least one radio-frequency antenna. The radio-frequency system shown here is merely schematically indicated. Typically, more than one pulse generation unit 15, more than one radio-frequency amplifier 19 and multiple radio-frequency antennas are used in a magnetic resonance apparatus 1.

Furthermore, the magnetic resonance apparatus 1 has gradient coils 21 with which magnetic gradient fields for (among other things) selective slice excitation and for spatial coding of the measurement signal are radiated in a measurement. The gradient coils 21 are controlled by a gradient coil control unit 23 that, like the pulse generation unit 15, is connected with the pulse sequence control unit 17.

The signals emitted by the excited nuclear spins are received by the body coil 13 and/or local acquisition coils 25, amplified by associated radio-frequency preamplifiers 27 and further processed and digitized by an acquisition unit 29.

With the use of a coil that can be operated both in transmission mode and in reception mode (for example the body coil 13), the correct signal relaying is regulated by an upstream transmission/reception diplexer 39.

A computer 37 that is connected with the magnetic resonance apparatus is supplied with the measurement data. From the acquired measurement data, the computer 37 generates MR images, projection images or even additional images that can be produced from the cited MR images or projection images, for example. The computer 37 is connected with a memory unit 35 such that the computer 37 can store, for example, intermediate results (for example using correction steps) of the processing of the measurement data in the memory unit 35 and also retrieve them again. Images generated from the measurement data can be presented to a user via an operator console 33 or be stored in the memory unit 35. The operator console 33 in particular comprises an input device 33.2—for example a keyboard and/or a pointer input device such as a computer mouse—for input of control commands by an operator at the computer 37 and other components of the magnetic resonance apparatus 1, for example the support device control unit 31, and a display device 33.1—for example at least one monitor—to display images created from acquired measurement data.

The computer 37 furthermore controls the individual system components, in particular during the acquisition of the measurement data. The computer 37 is fashioned so that the method according to the invention can be implemented with it. For this purpose, a computer-readable storage medium 40 according to the invention is installed on the computer 37 and is encoded with programming instructions that, when executed, cause a method according to the invention to be implemented by said computer 37.

The shown units, in particular the computer 37, the memory unit 35 and the different control units, should not necessarily be understood as a physical unit; rather, they can be composed of multiple sub-units that are possibly separately arranged spatially. As already mentioned, different methods are known for acquisition of measurement data of an examination region of a patient during a continuous travel of the examination region through a magnetic resonance apparatus. In the following the cited 2D axial measurements (data acquisitions) are discussed in detail. With these measurements the examination region is divided into and measured in slices that are situated perpendicular to the movement direction of the support device. In the simplest case, these slices are measured sequentially in the center of the magnetic resonance apparatus. In specific sequences (for example multishot sequences with a TR (TR: "repetition time") interval of a few tenths of a millisecond or longer) the sequential measurement requires a slow speed in the movement of the support device, which leads to long total measurement times and is therefore ineffective. One possibility to accelerate the measurement is to combine adjacent slices into slice stacks and to measure the slices of a slice stack in an interleaved manner (as in static measurement, i.e. without movement of the support device during the measurement). The slice stacks themselves are measured in succession. During the measurement of a slice, the measurement position follows a fixed anatomical position within the examination subject moving continuously with the support device. The speed with which the support device is hereby moved is selected such that a travel path during the time of the acquisition of a slice stack is equal to twice the extent of a slice stack. This results in corresponding slices in different slices stacks (for example the respective first, second, . . . slice) being measured identically. Conversely, different slices in a common slice stack are measured differently.

In particular, corresponding k-space lines of different slices of a slice stack are measured at different positions within the measurement volume of the magnetic resonance apparatus. Due to the (normally not ideally homogeneous) measurement conditions within the measurement volume, for example inhomogeneities of the basic magnetic field and/or nonlinearities of gradient fields, such measurements at different positions lead to different distortions of the MR images created from the measurement data. Discontinuities thereby arise in complete MR images composed of the individual MR images of the different slice stacks, in particular at the slice stack boundaries, since anatomically adjacent slices that were associated with different slice stacks take up different positions within their respective slice stack.

This problem does not occur in special 2D axial measurements with continuous movement of the examination subject, for example what is generally known as the "Sliding Multislice" (SMS) technique that, for example, is described in the article by Fautz and Kannengießer, "Sliding Multislice (SMS): A New Technique for Minimum FOV Usage in Axial Continuously Moving-Table Acquisitions", Magnetic Resonance in Medicine 55:363-370 (2006). This will be described in detail in the following.

In the SMS technique, the spatial frequency space (known as k-space) belonging to each slice of the real measurement volume is subdivided into S segments. The number N of slices that are measured during a TR interval of the underlying sequence is set equal to a whole-number multiple p of the number of segments:

$$N = p \cdot S, p \geq 1 \quad (1)$$

The slices of the examination region are now divided up into the p groups according to a specific pattern. If p is equal to two, for example, those slices of the examination region with even slice index are associated with the first group, and those slices of the slice stack with odd slice index are associated with the second group. A division of the slices into three or generally p groups ensues in an analogous manner, meaning that each third or, respectively, p-th slice of each slice stack is respectively associated with a group.

Furthermore, what is known as an active volume in the measurement volume of the magnetic resonance apparatus is selected. The extent of the active volume along the movement direction of the continuous movement is designed in the following as the active FOV. In the SMS technique the active FOV has an extent of N slice intervals d. This active FOV is now again subdivided into N/p=S equally large sections along the travel direction of the continuous movement of the support device (for example along the z-axis). The number of sections is therefore equal to the number of segments. The extent of a section is precisely p slice intervals d, where the slice interval d is the distance between adjacent slices. Each segment is now associated with a section of the active FOV. In this association, segments that contain k-space lines near the k-space center are advantageously associated with sections of the active FOV that have a small distance (in terms of absolute value) in the direction of the travel direction of the support device from the isocenter of the magnetic resonance apparatus.

TS=r·TR is now the time that is required for acquisition of the measurement data of a segment. TR is thereby the repetition time of the sequence used for the acquisition, and r is a whole number that depends on the sequence type. In echo train sequences such as turbo spin echo (TSE) sequences or echoplanar imaging (EPI) sequences, a complete segment is normally read out after a single excitation pulse and r is thus equal to one. In gradient echo sequences such as FLASH (Fast Low Angle Shot) or TrueFISP (True Fast Imaging with Steady state Precession), only one line per excitation pulse is read out and r is thus equal to the number of k-space lines per segment. Furthermore, TR is long enough that N slices can be excited, coded and read out in this time period.

A critical requirement to be able to implement the SMS technique is that the table feed during the acquisition time TS of a segment is precisely p slice intervals d between adjacent slices of the examination region. The table speed is thus:

$$v_{table} = \frac{p \cdot d}{r \cdot TR} = \frac{N \cdot d}{S \cdot r \cdot TR} \quad (2)$$

If this requirement is satisfied, the SMS measurement is implemented as described in the following for illustration with regard to FIG. 4:

The progressing positions in the z-direction (z-axis, here the direction of the continuous travel of the examination region; position z=0 corresponds to the center of the magnetic resonance apparatus) of three slice stacks $St_1$, $St_2$, $St_3$, each made of N=8 slices, are schematically plotted against multiples of the acquisition time of a segment TS in a diagram in FIG. 4. The division of the slices of the examination region into slice stacks here serves merely as an illustration. The first slice stack $St_1$ of the examination region enters directly into the active FOV of the magnetic resonance apparatus at the beginning of the measurement. Due to the conditions of the formulas (1) and (2), precisely p slices 1, 2 (here p=2) of the first slice stack $St_1$ enter into the first section S1 of the active FOV of the magnetic resonance apparatus during a first time interval $t_1$ of duration TS. During the first time interval $t_1=TS$, the k-space segment that is associated with the first section S1 of the active FOV is measured in these p slices 1, 2 of the first slice stack $St_1$. In the second time interval $t_2=2TS$, these p slices 1, 2 of the first slice stack $St_1$ enter into the second section S2 of the active FOV and the k-space segment that is associated with the second section S2 of the active FOV is acquired for the p slices 1, 2 of the first slice stack $St_1$. During the same second time interval $t_2$, the next p slices 3, 4 of the first slice stack $St_1$ (generally the p slices with slice index p+1, . . . , 2p) enter into the first section 51 of the active FOV. For these p slices 3, 4, the k-space segment that is associated with the first section S1 is acquired during the second time interval $t_2$ etc.

During the S-th interval of duration TS (here S=4), the last p slices 7, 8 of the first slice stack $St_1$ (generally the p slices with slice index N–p, . . . , N) enter into the first section S1 of the active FOV, and the first p slices 1, 2 of the first slice stack $St_1$ are located in the last section S4 of the active FOV. The data of the first p slices 1, 2 of the first slice stack $St_1$ are subsequently completely acquired. During the next time interval—thus after S+1 time intervals of duration TS, here $t_5=5TS$—the first p slices 1, 2 of the first slice stack $St_1$ have left the active FOV and the first p slices 1, 2 of the second slice stack $St_2$ enter into the first section S1 of the active FOV etc. It is noted that from the S-th time interval onwards measurement data of N segments in total are acquired per time interval TS or, respectively, that N slices are excited per repetition time TR.

Furthermore, it is noted that the most important sequence techniques that are compatible with the SMS technique are T1-weighted gradient echo sequences and T2-weighted turbo spin echo sequences. In both sequence techniques the acquisition of the measurement data for an MR image follows after multiple excitation pulses ("multi-shot techniques"), and the acquisition duration per MR image is long relative to typical time constants of human breathing (these are in the range from 3-10 seconds, for example). Therefore an acquisition of measurement data in the region of the abdomen and the lungs (thus in regions of a patient that are affected by breathing motion) cannot ensue with an SMS technique without additional measures.

In general, to avoid movement artifacts in examination regions affected by breathing that are caused by the breathing of the patient to be examined it is often necessary that the acquisition of measurement data in such an examination region affected by breathing motions of the patient is conducted under what is known as respiratory triggering. Regions affected by the breathing motion of the patient (for example regions near the lungs or the diaphragm) are at least part of the examination region to be examined, for example in whole-body examinations (for example in what are known as "screenings" in which, for example, persons without disease symptoms are examined from head to toe for possible undetected illnesses or their precursor stages) or in other examinations of, for example, the torso or portions of the torso of a patient to be examined.

In the case of respiratory triggering, the acquisition of the measurement data is synchronized with the quasi-periodical breathing movement so that the acquisition respectively occurs in an identical breathing phase. The periodic measurement pauses that thus occur, the durations of which depend on the individual breathing of the patient, are however not compatible with acquisitions given continuous travel of the support device (and therefore of the examination region). Therefore, this type of acquisition is only possible with a stationary support device. If an examination region to be examined is larger than a measurement volume of the magnetic resonance apparatus that is used, the examination region must be organized into sub-examination regions that fit into the measurement volume and are successively driven into the measurement volume (for example by means of the support device) in order to acquire respective measurement data there given a stationary support device).

Such a step-by-step acquisition of measurement data from examination regions of an examination region given a respectively stationary support device is also possible if the patient holds his or her breath, instead of by respiratory triggering. Each sub-region is hereby traversed in the measurement volume, and at the start of the acquisition the patient is asked to hold his breath until the acquisition of the measurement data for this sub-examination region has concluded. After acquisition of the measurement data of the sub-examination region the patient can breathe until the next examination region is moved into the measurement volume and the acquisition of measurement data of this sub-examination region begins. However, it is hereby problematical that the position of the sub-examination region can be shifted depending on how strongly the patient has inhaled or, respectively, exhaled before each holding of his breath, which can lead to gaps or overlaps between the examined sub-examination region in the complete MR image of the examination region that is created from the measurement data. For example, if a lesion is located in such a gap, this can be overlooked in the examination.

In order to enable such an interruption of the measurement and the travel and a later continuation of travel and measurement in acquisition techniques with continuous travel, sub-regions of the examination region that should be measured while the breath is held would have to be selected before the start of the measurement. In the aforementioned measurement techniques with continuous travel and organization of the examination region into slice stacks that are measured sequentially, such a sub-region may only comprise whole slice stacks. That only complete slice stacks can be selected in a sub-region given whose measurement the breath should be held severely limits the freedom in this selection. Moreover, the measurement is less efficient since a slice stack can contain slices that are affected by the breathing motion and others that are not affected or are only slightly affected by the breathing motion. After the sub-regions of the examination region are established, the magnetic resonance apparatus would have to be controlled such that the continuous travel and the measurement upon reaching such a sub-region are interrupted and are only continued again after administering a breath-hold command.

In the SMS technique described above, an additional problem that can drastically reduce the efficiency of the measurement occurs given the division of the slices into sub-regions that would have to be measured completely during a breath-hold interval. Given an interruption of the continuous travel after all segments of the last slice of the sub-region are measured, slices exist that border the sub-region and that were already partially measured but that have not traversed all sections of the active FOV during the continuous travel and therefore have no longer been completely acquired during the continuous travel. The same applies for measurement data of slices that border the next slice stack after a resumption of the continuous travel. Here slices are located in the active FOV that are associated with the preceding sub-region.

An attempt to nevertheless acquire measurement data of an examination region between diaphragm and pelvis by means of the SMS technique is published in the article by Sommer et al.: "Sliding Multislice MRI for Abdominal Staging of Patients With Pelvic Malignancies: A Pilot Study", Journal of Magnetic Resonance Imaging 27:666-672 (2008). There the acquisition of the measurement data is started beginning at the diaphragm, wherein an examined patient should hold his breath for 20 seconds so that the region of the examination region between diaphragm and pelvis that is affected by the breathing motion can be measured during this breath-hold period. For this the speed of the feed of the support device (on which the patient rests during the examination) must be selected high enough in order to have left the region of the examination region that is affected by the breathing movement promptly before resumption of the breathing of the patient. By the temporal placement of the breath-hold interval at the beginning of the measurement it is achieved that a typically deep breathing of the patient before the long breath-hold interval and a breath-hold command to the patient from an operator attending the measurement ensues to temporally match the breath-hold interval with the measurement before the measurement, and thus the entire acquisition of the measurement data can be implemented without interruption under continuous travel of the support device. However, it is furthermore problematical that—as shown above in formulas (1) and (2) for the SMS technique—the speed of the travel of the support device cannot be freely adjusted. Corresponding limitations of the speed of the travel apply in other techniques with continuous travel of the support device. This is primarily relevant due in part to significant limitations of the breath-hold capability in patients. In particular, often ill and/or old patients can hold their breath only for a few seconds. A breath-hold duration of 20 seconds can frequently not be achieved. Given acquisition under continuous travel of the support device, if movement artifacts should be avoided the maximum breath-hold duration must be sufficient to acquire measurement data of the examination region of the patient that is affected by the breathing. The (often short) maximum breath-hold duration thus leads to a higher necessary speed of the travel of the support device in order to be able to leave the examination region affected by the breathing in the short time of the breath-hold duration. This is normally done by a decrease of the resolution in the MR images generated from the acquired measurement data. Irregularities (for example lesions whose size falls below the achievable resolution) can thus not be detected. Additionally, a patient will normally breathe particularly deeply before and/or in particular after holding his breath, whereby movement artifacts at these points in time are disadvantageously intensified.

FIG. 2 shows a flowchart of an exemplary embodiment of an additional method to acquire measurement data of an examination region of a patient during a continuous travel of the examination region through a magnetic resonance apparatus for the generation of an image data set.

In a Step 101, the continuous travel of the support device and the acquisition of measurement data 105 during the continuous travel of the support device (and therefore during the continuous travel of the examination subject) is started. In the event that the examination region that is examined at the beginning of the measurement is an examination region affected by the breathing of the patient, to avoid movement artifacts the patient is already given a breath-hold command ("C") before the start of the continuous travel and the acquisition of measurement data in Step 101, i.e. the patient is asked to hold his or her breath, for example for a specific time duration. Otherwise the patient can breathe freely during the acquisition of the measurement data. A start according to Step 101 can in particular be initiated precisely like a resumption of the continuous travel that is described later.

The time duration for which the patient should hold his breath can thereby be largely freely predetermined, and thus be adapted to an individual breath-hold capability of the patient. A breath-hold command can thereby require the patient to hold his or her breath "as long as possible", for example, or until a corresponding, different command to cancel the breath-hold command is given to the patient. A maximum breath-hold duration that a patient is capable of therefore determines an upper limit for the predeterminable time duration, which is why the predeterminable time duration depends on the breath-hold duration possible for the patient. Such commands to the patient can be given to the patient either by an operator of the magnetic resonance apparatus who is attending the examination or also by an automatic speech output of the magnetic resonance apparatus (insofar as one is present).

The continuous travel of the support device and the acquisition of measurement data 105 is continued until the continuous travel is either manually interrupted ("m") or automatically interrupted after a predeterminable time duration ("t") in a next Step 102 after starting the continuous travel. Given such an interruption 102 of the continuous travel, the support device 9 is halted and moved back by a predeterminable distance counter to the travel direction of the continuous travel, meaning that the support device is automatically returned to a new starting position after its continuous travel was stopped.

Given an interrupted continuous travel, no measurement data are acquired for the generation of the image data set. Possible additionally acquired measurement data are not used for the generation of the image data set.

Such an interruption 102 of the continuous travel of the support device can be advantageously used for any preparation of an advantageous acquisition of measurement data in the portion of the examination region of the patient that is to be examined after the interruption of the continuous travel. In particular, during the interruption a patient can be prepared to hold his or her breath for an acquisition of additional measurement data 106 following the interruption. If the patient should already hold his or her breath before the interruption 102, the patient can use the interruption 102 in order to breathe freely ("B"), for example until a new breath-hold command ("C") is given to him.

After reaching the new start position, the resumption of the continuous travel is initiated (in particular manually ("m")) and additional measurement data 106 are acquired (Step 103). An operator of the magnetic resonance apparatus can hereby advantageously wait with the initiation of the resumption of the continuous travel until a patient could prepare for the new acquisition of measurement data, for example until the patient could breathe deeply before a breath-hold interval. An extensive gasping for air by the patient (for example at the end of a breath-hold interval, which otherwise often leads to artifacts as mentioned above in conventional system, can be avoided in this way. This is in particular avoided in that multiple short breath-hold commands can be given instead of one long one.

If the examination region that is examined after resumption of the measurement is an examination region affected by the breathing of the patient, to avoid movement artifacts a breath-hold command ("C") is already given to the patient before the resumption of the continuous travel and the acquisition of measurement data in Step 103, meaning that the patient is asked to hold his or her breath for a specific time duration, for example. The time duration for which the patient should hold his or her breath can be largely freely predetermined as described above, allowing the operator to take into account the individual breath-hold capability of the patient. The manual triggering of the resumption of the continuous travel facilitates a coordination of the administering of possible commands to the patient with the movement of the support device 9 and the acquisition of measurement data.

After resumption of the continuous travel it can be checked (Step 104) whether an additional interruption for the examination of the examination region is desired, in particular when (for example) measurement data of additional parts of the examination region that are likewise affected by a breathing movement of the patient should be acquired, and whether a new breath-hold command ("C") must be given in order to prevent movement artifacts in the acquired measurement data. If an additional interruption 102 is desired ("y"), the resumed continuous travel and the acquisition of measurement data 106 can again be interrupted manually ("m") or automatically after a predeterminable time duration ("t") after starting the continuous travel (new Step 102). If this is not the case ("n")—for example because the remaining examination region to be examined is not affected or is negligibly affected by the breathing movement—the continuous travel and the acquisition of the measurement data 106 can be continued until measurement data of the entire examination region have been acquired ("End"). An image data set ("BDS") is created from the acquired measurement data 105 and 106, for example by means of a computer 37 from FIG. 1.

Measurement data of an examination region affected by the breathing movement of the patient during a continuous travel of the examination region on a support device can if necessary be acquired in this way with multiple interruptions with a speed of the support device 9 that is optimal for the acquisition or the resolution in MR images reconstructed from the acquired measurement data, even if the acquisition of the measurement data of the examination region takes longer than the patient can hold his or her breath.

In order to halt the support device 9 after initiating the interruption 102, the travel of the support device must initially be braked. During this braking procedure the support device 9 covers an additional braking path $s_b$ in the direction of the continuous travel. The support device must likewise be initially accelerated to the speed desired for the continuous travel after initiating a resumption of the continuous travel. During this acceleration procedure the support device covers an acceleration path $s_{ac}$ in the direction of the continuous travel.

The predeterminable distance s by which the support device 9 is moved back after interruption of the continuous travel is advantageously at least as large as the added distances of the braking path $s_b$ accruing upon the interruption of the continuous travel and the acceleration path $s_{ac}$ accruing for the resumption of the continuous travel ($s=s_b+s_{ac}$). The continuous travel thus can be initiated again precisely at the position of the examination region in the magnetic resonance apparatus at which the examination region was located upon interruption of the continuous travel in the magnetic resonance apparatus. If this is desired, the distance s is provided as $s=s_b+s_{ac}$.

An actual return movement path of this distance s in the course of the measurement is advantageously automatically calculated, for example by a computer controlling the magnetic resonance apparatus from the values for $s_b$ and $s_{ac}$.

In another embodiment of the method, the acquisition of the measurement data ensues slice-by-slice, meaning that the examination region is divided into slices in which measurement data are acquired. Furthermore, the predeterminable distance s by which the support device is moved back after interruption of the continuous travel corresponds to added distances of a braking path accruing upon the interruption of the continuous travel and an acceleration path accruing for the resumption of the continuous travel, plus a whole-number multiple n of a distance d between two acquired slices ($s=s_b+s_{ac}+n*d$). After resumption of the continuous travel, measurement data of the n slices can thereby be acquired, from which n slices measurement data have already been acquired before the interruption of the continuous travel. Such "doubly" acquired measurement data can advantageously be used with added weighting in the generation of the image data set, for example in order to correct or to reduce artifacts caused by the interruption by changing the measurement conditions in the magnetic resonance apparatus. Additional exemplary embodiments for this purpose are described further below. If "doubly" acquired measurement data are desired, the distance s is provided as $s_b+s_{ac}+n*d$. An actual return travel path of this distance s is advantageously calculated automatically in the course of the measurement, for example by a computer controlling the magnetic resonance apparatus from the values for $s_b$, $s_{ac}$, n and d.

The continuous travel can be interrupted arbitrarily often. A breath-hold duration given a breath-hold command to the patient can likewise be very freely selected, and therefore the entire measurement can be individually adapted to the capabilities of the patient.

The time at which an interruption 102 of the continuous travel should be initiated, can be determined, for example using an overview image (known as a prescan) of the examination region, analogous to that obtained in a typical planning of an MR examination, for instance under consideration of the dimensions of the examination region and the speed of the continuous travel.

In another exemplary embodiment, an operator attending the examination manually initiates an interruption 102 of the continuous travel using a display of the progress of the acquisition of the measurement data during the continuous travel. A point in time of an interruption during the continuous travel can thus be controlled interactively by the operator of the magnetic resonance apparatus. Using such a display, the operator can recognize from which portion of the examination region measurement data are actually acquired and can decide with this information whether an interruption of the continuous travel—and therefore the acquisition of measurement data for the image data set for a sub-region of the examination region that is to be measured next—is desired, for instance because the patient should hold his breath for the sub-region to be measured next.

As a possible display of the progress of the acquisition of the measurement data, for example, a prevalent patient monitor can be selected, or a current position of the active FOV (i.e. the current position of the acquisition of the measurement data is displayed of the active FOV, thus the current position of the acquisition of the measurement data in a suitable overview image that, for example, was acquired in a conventional manner before the measurement (for instance within the scope of a prescan). Furthermore, a display of a current MR image from current or previously acquired measurement data is possible as a display of the progress of the acquisition of the measurement data. For example, a current overview image can be calculated (using "maximum intensity projection", MIP) from current MR images already reconstructed from the measurement data and is displayed to the operator as a projection image. However, it is disadvantageous that only those MR images for which all measurement data have already been acquired can be used for such a projection image. This leads to the situation that an already measured region is shown in the projection image, and not a region that is currently being measured. Furthermore, the reconstruction of the MR images from the already acquired measurement data can be complicated, in particular given the use of modern acquisition techniques such as parallel imaging, such that the (long) reconstruction time of the MR images leads to a further delay between the sub-region of the examination region that is shown in such an overview image and the currently measured sub-region. The display of such a projection image can therefore normally not be implemented fast enough, in particular not in real time (i.e. simultaneously with the actual progress of the acquisition of the measurement data).

FIG. 3 shows a flowchart of an exemplary embodiment of a method to display a progress of an acquisition of measurement data of an examination region of a patient during a continuous travel of the examination region through a magnetic resonance apparatus.

The acquisition of the measurement data and the continuous travel of the examination region through the magnetic resonance apparatus are started (Block 201), wherein the examination region is located at a first position (Pos. n=1). In the course of the entire measurement, measurement data are repeatedly acquired during the continuous travel, wherein the position of the examination region in the magnetic resonance apparatus changes with the continuous travel (Pos. n=n+1). In the acquisition of the measurement data, at least measurement data of the current portion of the examination region that is located in the measurement volume are retrieved from central k-space (Block 202) (where the measurement data for the current portion have been entered and stored). Based on this central k-space data, a current projection image of the current portion of the examination region that is located in the measurement value is calculated (Block 203), which currently calculated projection image is displayed on a display device (Block 205). In a simple exemplary embodiment, a current projection image can hereby be calculated via a one-dimensional Fourier transformation along a central k-space line of the currently acquired measurement data, wherein the readout direction is advantageously taken into account in the acquisition of the measurement data. That a projection of the measured subject can be acquired by Fourier transformation of a central k-space line (thus a k-space line through the center of k-space), wherein the projection direction in image space is oriented perpendicularly to the k-space line that is used, is already known from the "central slice theorem" (also called "Fourier slice theorem").

Since only measurement data from central k-space (in particular a central k-space line) are required for the calculation of current projection images, and the calculation can be implemented by means of a simple Fourier transformation, the calculation of the projection images can ensue extremely quickly.

If the aforementioned SMS technique is used for the acquisition of the measurement data for the generation of the image data set, as described above the central k-space line of a slice of the examination region is also measured in each time interval TS, and normally from the slice that traverses the center of the magnetic resonance apparatus during the time interval TS. A projection image of the slice of the examination region that is presently located at a specific location in the magnetic resonance apparatus (for example in its center) can now be calculated per time interval TS from this portion of the acquired measurement data (the measurement data that have been acquired along the central k-space line). It is noted that this projection image can be calculated before the data of the associated slice have been entirely acquired, which is only the case in the SMS technique if the associated slice leaves the active FOV of the magnetic resonance apparatus. Furthermore, the calculation of the projection image requires only a one-dimensional Fourier transformation along the central k-space line (one Fourier transformation per coil element used in the event that multiple coil elements are used for the acquisition of the measurement data) and is therefore extremely fast, even independent of whether parallel acquisition and reconstruction techniques that normally increase the reconstruction time are used or not.

The display of the progress of the acquisition of the measurement data thus changes continuously during the continuous travel, with newly acquired measurement data, and shows in real time from which portion of the examination region current measurement data are acquired. For this data, a progress image is advantageously constructed (Block 204) and displayed (Block 205) line-by-line from projection images calculated in succession in the course of the continuous travel of the examination region. Depending on the readout direction in k-space, the progress image can depict a coronal or sagittal projection of the examined examination region, for example. For example, each line of the progress image hereby corresponds to a calculated projection image. A progress image is thus shown little by little that displays not only the currently measured portion of the examination region but also already measured portions of the examination region. An observer of the progress image therefore receives a more comprehensive impression of the measurement that has already occurred.

In one exemplary embodiment, the acquisition of the measurement data ensues slice-by-slice, meaning that the examination region is divided into slices from which measurement data are acquired in succession. A projection image can hereby be calculated for every measured slice. A line in the progress image then corresponds to a slice of the examination region.

Since the examination region is divided into a known number of slices, the required number of slices of the progress image is also known. In Block 205 the progress image can thus already be displayed from the start of the measurement in full size, wherein lines that correspond to slices from which no measurement data have been acquired can, for example, be pre-populated with a pixel value of zero (which corresponds to a grey value of "black") until a projection image for the corresponding line has been calculated and the progress image is further developed in that the corresponding pixel values of the projection image are adopted for the pixels of the lines of the progress image. The progress image is thus continuously updated progressively from the current projection images in the course of the measurement. For example, in the case of the use of the SMS technique the progress image is thus extended once per time interval TS (for example by one additional line) and can be displayed in real time.

In a two-dimensional image (for example a progress image) there are two pixel intervals or spacings, thus two spacings between two adjacent pixels, namely one in the column direction and one in the line direction. A pixel is normally square, and therefore the pixel spacing in the line direction is the same as that in the column direction. If the examination region that is depicted as a whole is, for example, 400 mm in the column direction and the image has 256 columns, the pixel spacing in the column direction is thus $400/256$ mm=1.5625 mm. However, the examination region is divided into slices that are normally larger than 1.5625 mm (for example 5 mm), such that a progress image with square pixels in which each line corresponds to a measured slice of the examination region appears to be compressed. For a particularly illustrative display of the progress image, a pixel spacing between two adjacent lines of the progress image is therefore selected so that it corresponds to the pixel spacing of two adjacent pixels in the readout direction of the examination subject. The proportions of the examination region are thus also maintained in the displayed progress image. For example, this can be achieved by a linear interpolation. For example, a reformation can be implemented so that (for example) approximately 5 mm/1.5625 mm≈3 lines from the progress image correspond to each slice of the examination region. After such a reformation, the number of lines of the progress image is thus normally different than the number of slices in the examination region.

The display of a progress image constructed with the use of the "central slice theorem" using the SMS technique can not only ensue in real time but can even proceed "running ahead" since the measurement data for the calculation of a projection image are already available before the entire measurement data of a slice have been acquired. The simple (and therefore quickly possible) calculation of the projection images and the simple design of the progress image enables it to not lose this "advance" up to the display of the progress image, even given a use of more complex acquisition techniques and reconstruction methods.

FIG. 10 shows examples of possible progress images 300.1, 300.2, 300.3 at different times during the continuous travel. The measurement data have been acquired by means of the aforementioned SMS technique, wherein respectively only the central k-space data that were acquired in the central segments of the FOV were used for the calculation of the projection images. The examination region that is to be examined here respectively reaches from the head of the patient (top) to the thighs (bottom). A progress image 300.1 at an early point in time of the measurement is depicted to the left. As is visible, the progress image 300.1 is constructed from the head to the level of the shoulders. The acquisition of the measurement data of the examination region has thus progressed from the head to the level of the shoulders of the patient. The remaining lines of the progress image 300.1 are still populated with the value of zero and are therefore displayed in black. A progress image 300.2 at a later point in time during the measurement is depicted in the center. Here the acquisition of the measurement data has already progressed to the level of the hips of the patient. Finally, measurement data of the entire examination region are acquired in the progress image 300.3 depicted to the right, which in turn shows a later point in time just before the end of the measurement, and the progress image was constructed using the projection images of all slices of the examination region.

The display of a progress image 300.1, 300.2, 300.3 advantageously contains additional switching elements SE1, SE2, SE3 with which the display and/or the acquisition of the measurement data can be affected manually by activation, for example by clicking with the pointer input device. For example, the display of the progress image can be ended by means of the switching element SE1, and instead of this the display of another MR image (for example a preceding, reconstructed anatomical MR image data set from the acquired measurement data) can be switched to. For example, the acquisition of the measurement data and the continuous travel of the support device can be interrupted and/or resumed by means of switching elements SE2 and SE3.

For example, an actuation of switching element SE2 or SE3 given a continuous travel initiates an interruption of the continuous travel and the acquisition of measurement data.

Given an interrupted continuous travel, the resumption of the continuous travel can then be initiated again (for example via re-actuation of switching element SE2) until either measurement data of the entire examination region have been acquired and the measurement is ended or until the continuous travel and the acquisition of measurement data is interrupted again via re-actuation of switching element SE2 or SE3. If only regions of the examination region that are not affected by the breathing of the patient are still to be measured, the patient can also be instructed to continue to breathe normally before the resumption of the measurement via the switching element SE2. However, since the movement sensitivity of the examination region does not end abruptly, the operator can also instruct the patient to hold his or her breath in the next resumption of the measurement only as long as it is possible for the patient to do so comfortably, and after this the patient should continue to breathe smoothly and uniformly. This procedure prevents the patient from gasping for air at the end of a long breath-hold interval and thus from generating severe breathing movement. This procedure additionally has the consequence that this last breath-hold interval normally turns out to be shorter than the preceding, in which a severe "catching of one's breath" has no negative effect on the image quality due to the measurement pauses. Furthermore, the switching element SE2 is reasonably used to start the first measurement phase of the measurement (and therefore to initially start the continuous travel) insofar as the start of the examination region can be freely measured during breathing. For example, this is the case if the measurement begins at the head.

By activating switching element SE3 given an interrupted continuous travel (and measurement), the resumption of the continuous travel can, for example, be initiated for a predeterminable time duration that, for example, depends on a breath-hold duration that is possible for a patient. This is particularly advantageous if the maximum breath-hold duration of the patient is not sufficient to acquire measurement data of a contiguous portion of the examination region that is affected by the breathing of the patient. The measurement and the continuous travel are automatically re-interrupted after the predetermined time duration, the patient can breathe and the measurement can be resumed again after a new breath-hold command in order to measure the entire, contiguous examination region affected by the breathing step-by-step within the scope of the capabilities of the patient. The acquisition of measurement data of such a contiguous portion of the examination region that is affected by the breathing of the patient can thus be interrupted as often as necessary and be measured in sub-regions that correspond to the breath-hold capability of the patient. An interruption and a resumption of the measurement during continuous travel of the support device or of the examination region can hereby be controlled interactively or semi-automatically (SE3) by an operator.

Triggering of the resumption of the continuous travel and the measurement normally ensues only after the patient has been given time to breathe and the operator has, if necessary, given a breath-hold command for the acquisition of the measurement data after resumption of the measurement.

FIGS. 5 through 7 show illustrative diagrams for different exemplary embodiments of the method from FIG. 2 for the acquisition of measurement data of an examination region of a patient during a continuous travel of the examination region through a magnetic resonance apparatus for the generation of an image data set. FIGS. 5 through 7 are respectively analogous to the already described FIG. 4 and show exemplary embodiments using the SMS technique for the acquisition of the measurement data.

As discussed above, given an axial multi-slice measurement with continuous travel of the examination region through the magnetic resonance apparatus according to the SMS technique a division of the slices into sub-regions that are respectively completely measured in a phase with continuous table feed (thus for example in a breath-hold phase) is inefficient since, at the beginning and end of the continuous travel, slices that adjoin a preceding or a next sub-region and whose data cannot be completely acquired during the travel are located in the active FOV of the magnetic resonance apparatus. This can be avoided within the scope of the method according to the invention in that measurement data of a slice can also be acquired in different measurement phases, i.e. before and after an interruption of the measurement. This is explained in detail in the following.

FIG. 5 illustrates a particularly temporally efficient embodiment of the method in which the predeterminable distance s by which the support device is moved back after interruption of the continuous travel and before resumption of the continuous travel corresponds precisely to the added distances of a braking path accruing upon interruption of the continuous travel and an acceleration path accruing for the resumption of the continuous travel. After resumption of the continuous travel the measurement is thereby continued with the acquisition of measurement data of those slices and k-space positions corresponding to the sections S1, S2, S3, S4 that would also have been measured next given an uninterrupted travel.

However, this procedure can lead to artifacts since on the one hand the dynamic equilibrium state of the magnetization in the examination region is interrupted by the measurement pause after the interruption until the resumption of the continuous travel, and is only approximately achieved again after a transcendent phase after resumption of the measurement. Furthermore, the position of the diaphragm of the patient (and therefore also the position or, respectively, the elastic deformation of the adjoining organs) can differ before and after resumption of the continuous travel and the measurement— for example also given two successive measurements with breath held that are interrupted for a breathing by the patient—since the patient has respectively breathed deeply in a different manner, for example.

The type and severity of the resulting artifacts depends on a number of parameters, for example on the sequence technique that is used and the k-space trajectory that is used. Since, roughly speaking, the measurement data acquired in the acquisition of the measurement data in the center-proximal region of k-space determine the later image contrast and the measurement data acquired in the peripheral region of k-space determine the resolution, given use of the SMS technique the artifacts for such slices in which adjacent k-space lines that lie near the center are acquired in different measurement phases (i.e. before and after an interruption of the measurement and the continuous travel) are particularly noticeable.

As already mentioned, the inner k-space lines are preferably measured in connection with the SMS technique if the appertaining slice occupies the inner sections (thus sections S2 and S3 in the shown example) of the active FOV of the magnetic resonance apparatus. If adjacent lines in k-space are measured in temporal succession (known as linear k-space reordering, as used in FLASH sequences, for example) this, in connection with the SMS technique, has the result that a linear correlation between the k-space position and the measurement position in the magnetic resonance apparatus exists. This can be selected so that the inner k-space lines are associated with positions in the center. In FIGS. 4 through 7, the peripheral k-space lines would thus be associated with the SMS sections S1 and S4 and the inner k-space lines would be associated with the SMS sections S2 and S3.

In the embodiment shown in FIG. 5, the measurement is interrupted after the time interval $t_6$=6TS ("U") and—after a pause time TP during which the support device is moved back in order to compensate for the travel path during braking and acceleration phase, the patient possibly breaths and an operator subsequently gives a breath-hold command if necessary—the measurement of the slices that would also have been located in the active FOV of the system in the seventh time interval $t_7$ of duration TS given an uninterrupted travel is continued.

In the situation shown in FIG. 5, the inner k-space lines (in sections S2 and S3) of the slices 1 and 2 of the second slice stack $St_e$ are measured in different measurement phases—i.e. before the interruption U (S2) and after the interruption U (S3)—and are therefore particularly prone to artifacts.

FIG. 6 illustrates an additional embodiment that is less time-efficient but with which the artifacts just mentioned can normally be markedly reduced.

In contrast to the exemplary embodiment of FIG. 5, in this embodiment of the method the predeterminable distance s by which the support device is moved back after interruption of the continuous travel and before resumption of the continuous travel corresponds precisely to the added distances of a braking path accruing given the interruption of the continuous travel and an acceleration path accruing for the resumption of the continuous travel, plus a whole-number multiple n of the p-times the slice interval d increased (represented here with the values n=1, p=2, see description of the SMS technique above with regard to p). After resumption of the measurement and the continuous travel after an interruption U, measurement data are repeatedly measured from the slices that were located in the active FOV of the magnetic resonance apparatus in the last n time intervals of the duration TS before interruption of the measurement.

In FIG. 6 these are the slices 5, 6, 7, 8 of the first slice stack $St_1$ and the slices 1, 2, 3, 4 of the second slice stack $St_2$. In total r k-space lines of these slices are respectively measured in both measurement phases, thus before and after the interruption U.

In the exemplary embodiment of FIG. 7 the predeterminable distance s by which the support device is moved back after interruption of the continuous travel and before resumption of the continuous travel is increased again by p slice intervals relative to the exemplary embodiment of FIG. 6 (n=2). Here n·r=2·r k-space lines (that are associated with n SMS sections) of the slices that have been located in the active FOV of the MR system in the two last time intervals of duration TS before interruption of the measurement—thus the slices 5, 6, 7, 8 of the first slice stack $St_1$ and the slices 1, 2 of the second slice stack $St_2$—are respectively measured in both measurement phases. Moreover, r k-space lines of those slices that have been located only in an edge section S1 or S4 of the active FOV of the magnetic resonance apparatus in the last or, respectively, penultimate time interval of the duration TS before the interruption U of the measurement—thus in FIG. 7 the slices 3, 4 of the first slice stack $St_1$ (still in the penultimate time interval $t_5$ before the interruption U in section S4) and the slices 3, 4 of the second slice stack $St_2$ (for the first time in the last time interval $t_6$ before the interruption U in section S1)—are respectively measured repeatedly.

In further exemplary embodiments, the predeterminable distance s by which the support device is moved back after interruption of the continuous travel and before resumption of the continuous travel can be increased. This is increase in the distance s can be the added distances of a braking path accruing upon interruption of the continuous travel and an acceleration path accruing for the resumption of the continuous travel, plus a whole-number multiple n with n=N (N is the number of slices that are excited per TR interval and from which measurement data are acquired) of the slice interval d, i.e. $s=s_b+s_{ac}+N*d$. In this case the complete measurement data are acquired for every slice of the complete measurement data at least in one phase with continuous travel, whereby the described artifacts are avoided again. However, the acquisition time increases overall, and thus the efficiency of the method is reduced again. The distance s can thus be advantageously selected from the interval $[s=s_b+s_{ac}+N*d]$. A smaller distance s in particular supports the temporal efficiency of the method and a larger distance s reduces artifacts more and more. An actual return movement path of the distance s that is predetermined from the cited interval is advantageously calculated automatically from the values for $s_b$, $s_{ac}$, n and d during a measurement, for example by a computer controlling the magnetic resonance apparatus.

Measurement data measured repeatedly (i.e. in both measurement phases before and after the interruption U) can already be used to reduce the mentioned artifacts. Multiple possibilities hereby exist. A simple possibility is, for example, a weighted addition of the data measured twice in k-space:

$$s_{i,p}(k_y,k_x)=(1-w_{i,p}(k_y))\cdot s_{i,p}^a(k_y,k_x)+w_{i,p}(k_y)\cdot s_{i,p}^b(k_y,k_x),$$
$$0\leq w_{i,p}\leq 1 \quad (3)$$

wherein $s_{i,p}(k_y,k_x)$ designates the composite measurement data set that is subsequently additionally processed; $s_{i,p}^a(k_y,k_x)$ stands for the measurement data of the slice with slice index p and stack index i ($1\leq p\leq 8$, $1\leq i\leq 3$ in FIGS. 5 through 7) that are acquired in the first measurement phase (before the interruption U) and $s_{i,p}^b(k_y,k_x)$ stands for the measurement data of the slice with slice index p and stack index i ($1\leq p\leq 8$, $1\leq i\leq 3$ in FIGS. 5 through 7) that are acquired in the second measurement phase (after the interruption U). $w_{i,p}(k_y)$ is a function that assumes the values between zero and one, and $k_y$ determines the relative weighting between second and first measurement phase for each k-space line. In the selection of the weighting function a large degree of freedom exists as long as the following criteria are satisfied:

a. $w_{i,p}(k_y)=0$ for those k-space lines $k_y$ that are measured only in the first measurement phase.

b. $w_{i,p}(k_y)=1$ for those k-space lines $k_y$ that are measured only in the second measurement phase.

c. The curve of $w_{i,p}(k_y)$ is smooth, or, expressed mathematically:

$$|w_{i,p}(k_y+\Delta k_y)-w_{i,p}(k_y)|<<1, \forall k_y,$$

wherein $\Delta k_y$ is the k-space interval of two adjacent lines, the symbol "<<" stands for "small relative to" and the symbol "$\forall$" means "for all".

d. $w_{i,p}(k_y)$ assumes small values for k-space lines that are measured during the transcendent state at the beginning of the second measurement phase.

Figure 8:
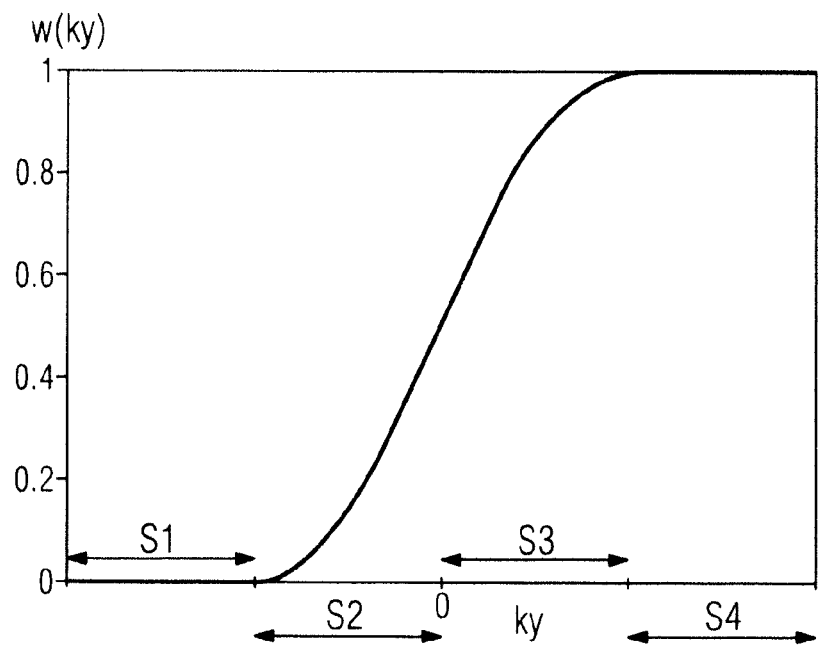
FIGS. 8-9 show examples of weighting functions for a weighted, added use of repeatedly acquired measurement data for the generation of the image data set.
Figure 9:
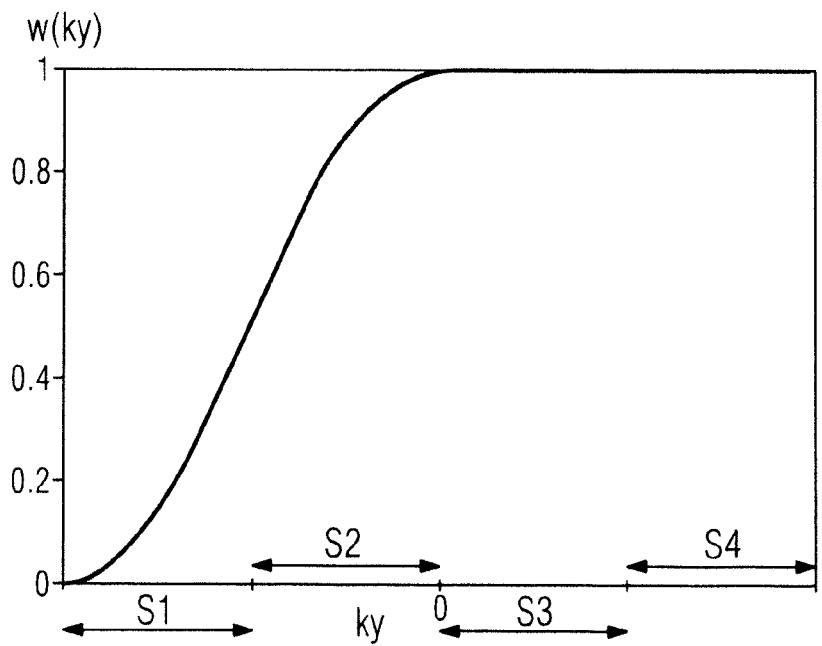

FIGS. 8 and 9 show possible weighting functions $w_{i,p}(k_y)$ for a weighted added use of repeatedly acquired measurement data for the generation of the image data set.

FIG. 8 shows an example for selection of the weighting function $w_{1,7}$ and $w_{1,8}$ of slices 7 and 8 of the first slice stack $St_1$ from FIG. 7. Linear k-space reordering is thereby assumed. The k-space lines that are associated with the first section S1 of the active FOV are measured only in the first measurement phase for these two slices. The value of the weighting functions $w_{1,7}$ and $w_{1,8}$ for these k-space lines is accordingly equal to zero. The central k-space lines that are associated with sections S2 and S3 are measured during both measurement phases. The weighting functions $w_{1,7}$ and $w_{1,8}$ increases from zero to one in the shape of a cosine function in this range. The k-space lines that are associated with the fourth section S4 are measured only in the second measurement phase. The weighting function $w_{1,7}$ or, respectively, $w_{1,8}$ is accordingly equal to one in this range.

FIG. 9 shows as an example a possible, corresponding selection of the weighting functions $w_{2,1}$ and $w_{2,2}$ of slices 1, 2 of the second slice stack $St_2$ from FIG. 7. For these two slices the k-space lines associated with sections S1 and S2 of the active FOV are measured repeatedly. Therefore the weighting functions $w_{2,1}$ and $w_{2,2}$ in this range increase in the shape of a cosine function from zero to one. The k-space lines that are associated with the third and fourth section S3 and S4 are measured only in the second measurement phase. The weighting functions $w_{2,1}$ and $w_{2,2}$ in this range are accordingly equal to one.

Since these two slices 1, 2 of the second slice stack $St_2$ are measured completely in the second measurement phase, the following alternative selection of the weighting function is suggested:

$$w_{2,1}(k_y)=w_{2,2}(k_y)=1, \forall k_y.$$

This means that data of these two slices that are measured during the first measurement phase are completely discarded and the two slices are measured completely in a breath-hold phase, as in the breath-hold techniques in conventional MR measurements without continuous travel of the support devise. This is advantageous insofar as the position of the diaphragm of the patient may differ in the two measurement phases. However, given approximately identical diaphragm positions during the two measurement phases the first alternative (FIG. 9) leads to images with higher signal-to-noise ratio (SNR). Furthermore, the second selection (constant weighting function equal to one) severely breaks criterion d. For these two slices 1, 2, however, the peripheral k-space lines are measured at the beginning of the second measurement phase. At best a slight edge exaggeration is thus to be accepted in the image, which has less of a negative effect on the image impression than a discontinuity in the central region of k-space.

Measurement data measured repeatedly (i.e. before and after the interruption U) can be used for additional purposes.

For example, repeatedly measured measurement data can be used in order to establish with image processing techniques whether the patient has realized similar breath-hold states (thus similar positions of his diaphragm) or not in both measurement phases. If the diaphragm position in both measurement phases is similar, the measurement data are identical apart from effects as a result of the transcendent state of the magnetization at the beginning of the second measurement phase and physiological procedures such as heart movement or peristalsis. In this case a degree of correlation either directly between the doubly measured central k-space data or between images that are calculated from these data with the aid of a Fourier transformation is large enough. Conversely, different breath-hold positions can be concluded from a low value of the degree of correlation. For example, this information can then be used to automatically select the optimal weighting function, for example for the slices 1, 2 of the second slice stack $St_2$ from FIG. 7. Given a high degree of correlation, for example, a weighting function as shown in FIG. 9 could be selected; given a low degree of correlation, a constant weighting function $w_{2,1}(k_y)=w_{2,2}(k_y)=1, \forall k_y$ could be selected.

Furthermore, repeatedly measured measurement data can be used to respectively reconstruct an MR image with different weightings, for example from the respective acquired central k-space data. For example, a first MR image can be reconstructed whereby measurement data acquired in the first measurement phase before the interruption is given a high weighting and a second MR image can be reconstructed with the measurement data acquired in the second measurement phase, after the interruption, being given a high weighting. In particular given different breath-hold positions before and after the interruption, gaps in the examination region that arise due to these different breath-hold positions can be closed or reduced. The danger that, for example, a lesion is overlooked in such a gap can therefore be reduced.

Furthermore, as described above a degree of correlation between repeatedly measured measurement data of a slice can be calculated and—insofar as the corresponding k-space data were also acquired in a neighboring slice adjacent to this slice—a degree of correlation between these nominally different slices—thus for example the slice and its neighboring slice—can furthermore be calculated. If the calculated degree of correlation between two nominally different slices is greater than the degree of correlation between nominally identically slices, this indicates that the slice of the examination region has migrated due to the different breath-hold position in the magnetic resonance apparatus (independent of the continuous travel). In such a case, the composition of measurement data that were measured at nominally different positions before and after the interruption possibly leads to a better result than the composition of measurement data that were measured at nominally identical slice positions. A weighted addition for such a composition from Formula (3) would hereby be replaced by the following weighted addition, for example:

$$s_{i,p}(k_y,k_x)=(1-w_{i,p}(k_y))\cdot s_{\tilde{i},\tilde{p}}^a(k_y,k_x)+w_{i,p}(k_y)\cdot s_{i,p}(k_y,k_x),$$
$$0\leq w_{i,p}\leq 1.$$

$\tilde{i}, \tilde{p}$ is thereby the stack index or slice index of the slice whose measurement data measured before the interruption maximizes the degree of correlation with corresponding measurement data of the slice with stack index i and slice index p that are measured after the interruption.

Although modifications and changes may be suggested by those skilled in the art, it is the intention of the inventor to embody within the patent warranted hereon all changes and modifications as reasonably and properly come within the scope of his contribution to the art.

The invention claimed is:

1. A method to display progress of acquisition of magnetic resonance measurement data from an examination region of an examination subject, comprising the steps of:
 continuously moving an examination subject, comprising an examination region, through a magnetic resonance data acquisition apparatus in a feed direction and, with said magnetic resonance data acquisition apparatus, successively acquiring magnetic resonance measurement data from the examination region of the examination subject during continuous travel of the examination region through the magnetic resonance apparatus;
 entering current axial magnetic resonance measurement data, acquired in a plane of the subject that is orthogonal to said feed direction, into k-space, comprising a central k-space region, in a memory during the continuous travel of the examination region through the magnetic resonance data acquisition apparatus;
 from a processor, accessing said memory and automatically calculating a current coronal or sagittal projection image of the examination region based on said current axial measurement data in said central k-space region during said continuous travel of the examination region through the magnetic resonance data acquisition apparatus; and
 displaying the current coronal or sagittal projection image contemporaneously with calculation thereof by said processor.

2. A method as claimed in claim 1 comprising entering said current magnetic resonance measurement data into said memory in a plurality of k-space lines in k-space, including a central k-space line in said central region of k-space, and calculating said current projection image in said processor as a one-dimensional Fourier transformation along said central k-space line of the current magnetic resonance measurement data.

3. A method as claimed in claim 1 comprising acquiring said current magnetic resonance measurement data slice-by-slice from said examination region, and calculating said current projection image for each slice.

4. A method as claimed in claim 1 comprising acquiring said magnetic resonance measurement data using an SMS technique.

5. A method as claimed in claim 1 comprising, in said processor, constructing and displaying a progress image from successive projection images calculated during the continuous travel of the examination region through the magnetic resonance data acquisition apparatus.

6. A method as claimed in claim 5 wherein said progress image is comprised of pixel values arranged in lines and columns, and comprising pre-populated lines of said progress image with respective pixel values of zero until a projection image corresponding to that line is calculated, and a further progress image is constructed in which that line is filled with pixel values of the projection image.

7. A method as claimed in claim 5 wherein said progress image is comprised of pixel arranged in lines and columns, and comprising constructing said progress image with a pixel spacing between two adjacent lines of said progress image corresponding to a pixel spacing between two adjacent pixels in a readout direction of said magnetic resonance measurement data in said magnetic resonance data acquisition apparatus.

8. A magnetic resonance apparatus to display progress of acquisition of magnetic resonance measurement data from an examination region of an examination subject, comprising:
 a magnetic resonance data acquisition unit;
 a subject support mounted for movement through said data acquisition unit in a feed direction, said subject support being adapted to support an examination subject, comprising an examination region, thereon;
 a computerized operating system configured to operate said subject support and said data acquisition unit to continuously move the examination subject on the subject support through the data acquisition unit in said feed direction and, with said magnetic resonance data acquisition unit to successively acquire magnetic resonance measurement data from the examination region of the examination subject during continuous travel of the examination region through the magnetic resonance unit;
 a memory;
 said operating system being configured to enter current axial magnetic resonance measurement data, acquired in a plane of the subject that is orthogonal to said feed direction, into k-space in said memory, comprising a central k-space region, during the continuous travel of the examination region through the magnetic resonance data acquisition apparatus;

said operating system comprising a processor configured to access said memory and automatically calculate a current coronal or saqittal projection image of the examination region based on said current axial measurement data in said central k-space region during said continuous travel of the examination region through the magnetic resonance data acquisition apparatus; and a display in communication with said processor at which said processor displays the current coronal or sagittal projection image contemporaneously with calculation thereof by said processor.

9. A non-transitory computer-readable storage medium encoded with programming instructions, said storage medium being loadable into a computerized operating and data processing system of a magnetic resonance apparatus, and said programming instructions causing said computerized operating and data processing system to:

continuously move a subject support with an examination subject thereon, said examination subject comprising an examination region, through a magnetic resonance data acquisition unit of the magnetic resonance apparatus in a feed direction and to operate said magnetic resonance data acquisition unit to successively acquire magnetic resonance measurement data from the examination region of the examination subject during continuous travel of the examination region through the magnetic resonance apparatus;

enter current axial magnetic resonance measurement data, acquired in a plane of the subject that is orthogonal to said feed direction, into k-space, comprising a central k-space region, in a memory during the continuous travel of the examination region through the magnetic resonance data acquisition unit;

access said memory and automatically calculate a current coronal or sagittal projection image of the examination region based on said current measurement data in said central k-space region during said continuous travel of the examination region through the magnetic resonance data acquisition apparatus; and display the current coronal or sagittal projection image contemporaneously with calculation thereof.

* * * * *